(12) United States Patent
Adams et al.

(10) Patent No.: US 6,770,739 B1
(45) Date of Patent: Aug. 3, 2004

(54) ENHANCERS OF CFTR CHLORIDE CHANNEL FUNCTION

(75) Inventors: Lynn Adams, Cleveland Heights, OH (US); Pamela B. Davis, Cleveland Heights, OH (US); Jian Jie Ma, Highland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/512,260

(22) Filed: Feb. 24, 2000

Related U.S. Application Data

(60) Provisional application No. 60/121,495, filed on Feb. 24, 1999.

(51) Int. Cl.[7] .......................... C07K 14/00; C07H 21/00
(52) U.S. Cl. ........................ 530/300; 530/350; 536/23.4
(58) Field of Search ................................ 530/300, 350; 536/23.4; 514/12, 2

(56) References Cited

U.S. PATENT DOCUMENTS 5,776,677 A  * 7/1998 Tsui et al. ...................... 435/6
6,025,140 A  * 2/2000 Langel et al. .................. 435/6

FOREIGN PATENT DOCUMENTS

WO    WO 95/25796    9/1995

OTHER PUBLICATIONS

Adams et al. "Deletion of a negatively charged region from the R domain of CFTR alters PKA–dependent regulation fo the CFTR channel" Biophysical Journal, vol. 74, No. 2 Part 2, Feb. 1998, p. A344 (Abstract).

Tasch et al. "Functional dissection of the R domain of cystic fibrosis transmembrane conductance regulator" FEBS Letters vol. 445, No. 1, Feb. 19, 1999, pp. 63–68.

Winter et al. "Stimulation of CFTR activity by its phosphorylated R domain" Nature, vol. 389, No. 6648, 1997, pp. 294–296.

Ma et al. "Phosphorylation–dependent block of cystic fibrosis transmembrane condcutance regulator chloride channel by exogenous R domain protein" Journal of Biological chemistry, vol. 271, No. 13, 1996, pp. 7351–7356.

Ma et al. "Function of the R domain in the cystic fibrosis transmembrane conductance regulator chloride channel" Journal of Biological Chemistry, vol. 272, No. 44, Oct. 31, 1997, pp. 28133–28141.

Cotten et al. "Covalent modification of the regulatory domain irreversibly stimulates cystic fibrosis transmembrane conductance regulator" Journal of Biological chemistry, vol. 272, No. 41, 1997, pp. 25617–25622.

Rich et al. "Regulationof the cystic fibrosis transmembrane conductance regulator cheloride channel by negative charge in the R domain" Journal of Biological Chemistry, vol. 268, No. 27, 1993, pp. 20259–20267.

* cited by examiner

*Primary Examiner*—Yvonne Eyler
*Assistant Examiner*—Regina M. DeBerry
(74) *Attorney, Agent, or Firm*—Banner & Witcoff, Ltd.

(57) ABSTRACT

Phosphorylation of the cystic fibrosis transmembrane conductance regulator (CFTR) by cyclic AMP-dependent protein kinase (PKA) is essential for opening the CFTR chloride channel. A short segment containing many negatively charged amino acids (817–838, NEG2) within the regulatory (R) domain of CFTR is a critical regulator of the chloride channel activity. Deletion of NEG2 from CFTR completely eliminates the PKA dependence of the chloride channel. Exogenous NEG2 peptide interacts with the CFTR molecule and exhibits stimulatory effects on CFTR function. Our data suggest that NEG2 interacts with other cytosolic domains of CFTR to control the opening transitions of the chloride channel.

9 Claims, 4 Drawing Sheets

FIG. IA

NEG1  $^{725}$EEDSDEPLE$^{733}$

NEG2  $^{817}$GLEISEEINEEDLKECFFDD$\underline{D}$ME$^{838}$

SEQUENCE LISTING

```
<160> NUMBER OF SEQ ID NOS: 6

<210> SEQ ID NO 1
<211> LENGTH: 18
<212> TYPE: PRT
<213> ORGANISM: Homo sapiens

<400> SEQUENCE: 1

Gly Leu Glu Ile Ser Glu Glu Ile Asn Glu Glu Asp Leu Lys Glu Cys
 1               5                  10                  15

Phe Phe

<210> SEQ ID NO 2
<211> LENGTH: 22
<212> TYPE: PRT
<213> ORGANISM: Homo sapiens

<400> SEQUENCE: 2

Gly Leu Glu Ile Ser Glu Glu Ile Asn Glu Glu Asp Leu Lys Glu Cys
 1               5                  10                  15

Phe Phe Asp Asp Met Glu
            20

<210> SEQ ID NO 3
<211> LENGTH: 559
<212> TYPE: PRT
<213> ORGANISM: HSV-1

<400> SEQUENCE: 3

Met Ala Arg Phe His Arg Pro Ser Glu Asp Glu Asp Tyr Glu Tyr
 1               5                  10                  15

Ser Asp Leu Trp Val Arg Glu Asn Ser Leu Tyr Asp Tyr Glu Ser Gly
                20                  25                  30

Ser Asp Asp His Val Tyr Glu Glu Leu Arg Ala Ala Thr Ser Gly Pro
            35                  40                  45

Glu Pro Ser Gly Arg Arg Ala Ser Val Arg Ala Cys Ala Ser Ala Ala
        50                  55                  60

Ala Val Gln Pro Ala Ala Arg Gly Arg Asp Arg Ala Ala Ala Gly
 65                 70                  75                  80

Thr Thr Val Ala Ala Pro Ala Ala Pro Ala Arg Arg Ser Ser Ser
                85                  90                  95

Arg Ala Ser Ser Arg Pro Pro Arg Ala Ala Ala Asp Pro Val Leu
                100                 105                 110

Arg Pro Ala Thr Arg Gly Ser Ser Gly Gly Ala Gly Ala Val Ala Val
            115                 120                 125

Gly Pro Pro Arg Pro Arg Ala Pro Pro Gly Ala Asn Ala Val Ala Ser
        130                 135                 140
```

-continued

```
Gly Arg Pro Leu Ala Phe Ser Ala Ala Pro Lys Thr Pro Lys Ala Pro
145                 150                 155                 160

Trp Cys Gly Pro Thr His Ala Tyr Asn Arg Thr Ile Phe Cys Glu Ala
                165                 170                 175

Val Ala Leu Val Ala Ala Glu Tyr Ala Arg Gln Ala Ala Ser Val
            180                 185                 190

Trp Asp Ser Asp Pro Pro Lys Ser Asn Glu Arg Leu Asp Arg Met Leu
            195                 200                 205

Lys Ser Ala Ala Ile Arg Ile Leu Val Cys Glu Gly Ser Gly Leu Leu
    210                 215                 220

Ala Ala Ala Asn Asp Ile Leu Ala Ala Arg Ala Gln Arg Pro Ala Ala
225                 230                 235                 240

Arg Gly Ser Thr Ser Gly Gly Glu Ser Arg Leu Arg Gly Glu Arg Ala
                245                 250                 255

Arg Pro Met Thr Ser Arg Arg Ser Val Lys Ser Gly Pro Arg Glu Val
                260                 265                 270

Pro Arg Asp Glu Tyr Glu Asp Leu Tyr Tyr Thr Pro Ser Ser Gly Met
            275                 280                 285

Ala Ser Pro Asp Ser Pro Pro Asp Thr Ser Arg Arg Gly Ala Leu Gln
            290                 295                 300

Thr Arg Ser Arg Gln Arg Gly Glu Val Arg Phe Val Gln Tyr Asp Glu
305                 310                 315                 320

Ser Asp Tyr Ala Leu Tyr Gly Gly Ser Ser Glu Asp Asp Glu His
                325                 330                 335

Pro Glu Val Pro Arg Thr Arg Pro Val Ser Gly Ala Val Leu Ser
            340                 345                 350

Gly Pro Gly Pro Ala Arg Ala Pro Pro Pro Ala Gly Ser Gly Gly
            355                 360                 365

Ala Gly Arg Thr Pro Thr Thr Ala Pro Arg Ala Pro Arg Thr Gln Arg
    370                 375                 380

Val Ala Thr Lys Ala Pro Ala Ala Pro Ala Ala Glu Thr Thr Arg Gly
385                 390                 395                 400

Arg Lys Ser Ala Gln Pro Glu Ser Ala Ala Leu Pro Asp Ala Pro Ala
                405                 410                 415

Ser Thr Ala Pro Thr Arg Ser Lys Thr Pro Ala Gln Gly Leu Ala Arg
                420                 425                 430

Lys Leu His Phe Ser Thr Ala Pro Pro Asn Pro Asp Ala Pro Trp Thr
                435                 440                 445

Pro Arg Val Ala Gly Phe Asn Lys Arg Val Phe Cys Ala Ala Val Gly
    450                 455                 460

Arg Leu Ala Ala Met His Ala Arg Met Ala Ala Val Gln Leu Trp Asp
465                 470                 475                 480

Met Ser Arg Pro Arg Thr Asp Glu Asp Leu Asn Glu Leu Leu Gly Ile
                485                 490                 495

Thr Thr Ile Arg Val Thr Val Cys Glu Gly Lys Asn Leu Leu Gln Arg
                500                 505                 510

Ala Asn Glu Leu Val Asn Pro Asp Val Val Gln Asp Val Asp Ala Ala
            515                 520                 525

Thr Ala Thr Arg Gly Arg Ser Ala Ala Ser Arg Pro Thr Glu Arg Pro
    530                 535                 540

Arg Ala Pro Ala Arg Ser Ala Ser Arg Pro Arg Arg Pro Val Glu
545                 550                 555
```

-continued

```
<210> SEQ ID NO 4
<211> LENGTH: 27
<212> TYPE: PRT
<213> ORGANISM: Artificial Sequence
<220> FEATURE:
<223> OTHER INFORMATION: membrane permeating peptide

<400> SEQUENCE: 4

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 5
<211> LENGTH: 16
<212> TYPE: PRT
<213> ORGANISM: Artificial Sequence
<220> FEATURE:
<223> OTHER INFORMATION: membrane permeating peptide

<400> SEQUENCE: 5

Arg Gln Ile Lys Ile Trp Phe Gln Asn Arg Arg Met Lys Trp Lys Lys
 1               5                  10                  15

<210> SEQ ID NO 6
<211> LENGTH: 9
<212> TYPE: PRT
<213> ORGANISM: Homo Sapiens

<400> SEQUENCE: 6

Glu Glu Asp Ser Asp Glu Pro Leu Glu
 1               5
```

ENHANCERS OF CFTR CHLORIDE CHANNEL FUNCTION

Figure 1B:
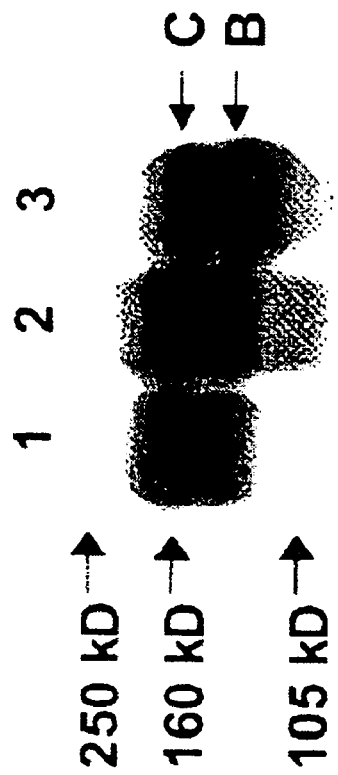

This application claims the benefit of co-pending provisional application Serial No. 60/121,495, filed Feb. 24, 1999, which is incorporated by reference herein.

This invention was made with government support under RO1 HL/DK 49003, P30 DK27651 and RO1 DK51770 awarded by the National Institute of Health. The government has certain rights in the invention.

TECHNICAL FIELD OF THE INVENTION

This invention is related to the field of cystic fibrosis. More particularly, it is related to the area of therapeutic treatments and drug discovery for treating cystic fibrosis.

BACKGROUND OF THE INVENTION

Defects in CFTR, a chloride channel located in the apical membrane of epithelial cells, are associated with the common genetic disease, cystic fibrosis (Quinton, 1986, Welsh and Smith, 1993, Zielenski and Tsui, 1995). CFTR is a 1480 amino acid protein that is a member of the ATP binding cassette (ABC) transporter family (Riordan et al., 1989, Higgins, 1992). Each half of CFTR contains a transmembrane domain and a nucleotide binding fold (NBF), and the two halves are connected by a regulatory, or R domain. The R domain is unique to CFTR and contains several consensus PKA phosphorylation sites (Cheng et al., 1991, Picciotto et al., 1992).

Opening of the CFTR channel is controlled by PKA phosphorylation of serine residues in the R domain (Tabcharani et al., 1991, Bear et al., 1992) and ATP binding and hydrolysis at the NBFs (Anderson et al., 1991, Gunderson and Kopito, 1995). Phosphorylation adds negative charges to the R domain, and introduces global conformational changes reflected by the reduction in the α-helical content of the R domain protein (Dulhanty and Riordan, 1994). Thus, electrostatic and/or allosteric changes mediated by phosphorylation are likely to be responsible for interactions between the R domain and other CFTR domains that regulate channel function (Rich et al., 1993, Gadsby and Naim, 1994).

Rich et al., 1991 showed that deletion of amino acids 708–835 from the R domain (ΔR-CFTR), which removes most of the PKA consensus sites, renders the CFTR channel PKA independent, but the open probability of ΔR-CFTR is one-third that of the wild type channel and does not increase upon PKA phosphorylation (Ma et al., 1997, Winter and Welsh, 1997). Thus, it is possible that deletion of the R domain removes both inhibitory and stimulatory effects conferred by the R domain on CFTR chloride channel function. This conclusion is supported by studies that show that addition of exogenous unphosphorylated R domain protein (amino acids 588–858) to wt-CFTR blocks the chloride channel (Ma et al., 1996), suggesting that the unphosphorylated R domain is inhibitory. Conversely, exogenous phosphorylated R domain protein (amino acids 588–855 or 645–834) stimulated the ΔR-CFTR channel, suggesting that the phosphorylated R domain is stimulatory (Ma et al., 1997, Winter and Welsh, 1997). Therefore, it appears that the manifest activity (stimulatory or inhibitory) depends on the phosphorylation state of the R domain.

About 25% of the known 700 mutations in CFTR produce a mutant CFTR protein which is properly transported to the apical membrane of epithelial cells but have only low level, residual channel activity. There is a need in the art for agents which can boost the level of channel activity in those mutants having low level activity.

SUMMARY OF THE INVENTION

It is an object of the present invention to provide an isolated polypeptide useful for enhancing the open probability of CFTR chloride channels.

It is another object of the present invention to provide a method of activating a CFTR protein to enhance its open probability.

These and other objects of the invention are achieved by providing one or more of the embodiments described below. In one embodiment of the invention an isolated polypeptide is provided. The polypeptide comprises a portion of CFTR (cystic fibrosis transmembrane conductance regulator) protein of between 10 and 100 amino acids, said portion comprising 18 amino acids as shown in SEQ ID NO: 1.

In another embodiment of the invention a method is provided for activating a CFTR protein. A polypeptide is applied to a CFTR protein which forms a cAMP regulated chloride channel. The polypeptide consists of a portion of CFTR protein which comprises 18 amino acids as shown in SEQ ID NO: 1, whereby the open probability of the channel formed by the CFTR increases by at least 25%.

According to another aspect of the invention a method is provided for activating a CFTR protein. A polypeptide is applied to a CFTR protein which forms a cAMP regulated chloride channel. The polypeptide consists of a portion of CFTR protein which comprises 22 amino acids as shown in SEQ ID NO: 2, whereby the open probability of the channel formed by the CFTR increases by at least 25%.

The present invention thus provides the art with reagents and tools for enhancing function of channels which are defective in cystic fibrosis patients.

DETAILED DESCRIPTION OF THE DRAWINGS

FIG. 1. Deletion of Negatively Charged Regions from the R Domain Results in Expression of Mature Glycosylated, Phosphorylatable CFTR Proteins (FIG. 1A) Sequences of NEG1 and NEG2 within the R domain. Residues where mutations have been identified in the CFTR cDNA are underlined (E822K, E826K, D836Y).

(FIG. 1B) NEG2 is predicted to form an amphipathic α-helix as determined by secondary structure determination (Geourjon and Deleage, 1995, Rost and Sander, 1993, Rost and Sander, 1994) and illustrated in this space filling model. Negatively charged residues are colored pink, and the positively charged lysine is colored green.

(FIG. 1C) In vitro phosphorylation of wt-(lane 1), ΔNEG1-(lane 2) and ΔNEG2-CFTR (lane 3) by PKA in the presence of $\gamma y$-$^{32}$P-ATP. Both the core (band B) and fully glycosylated (band C) forms of all three CFTR molecules are phosphorylated.

Figure 2A:
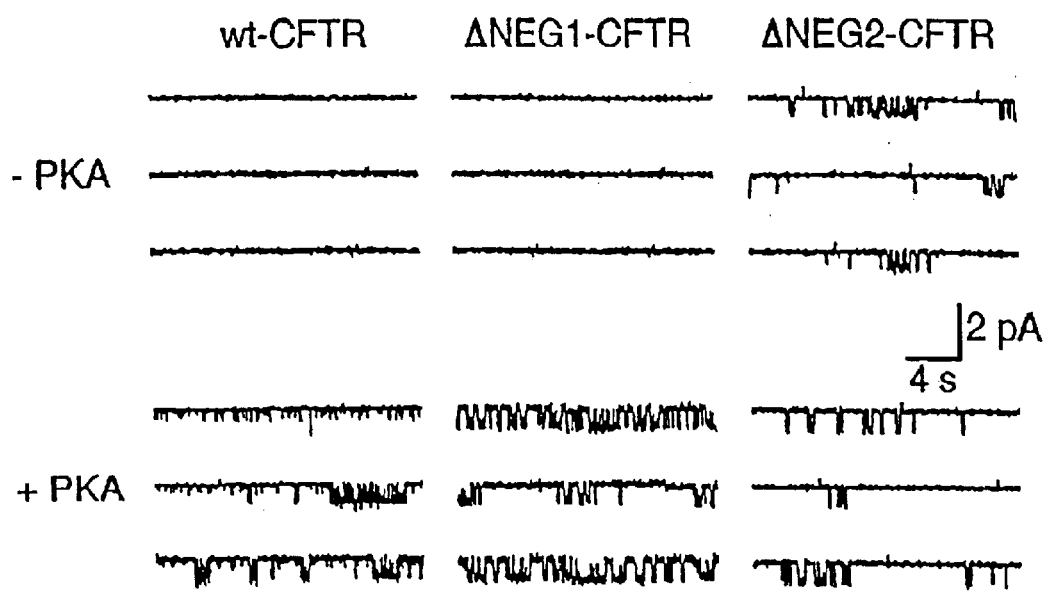
Figure 2B:
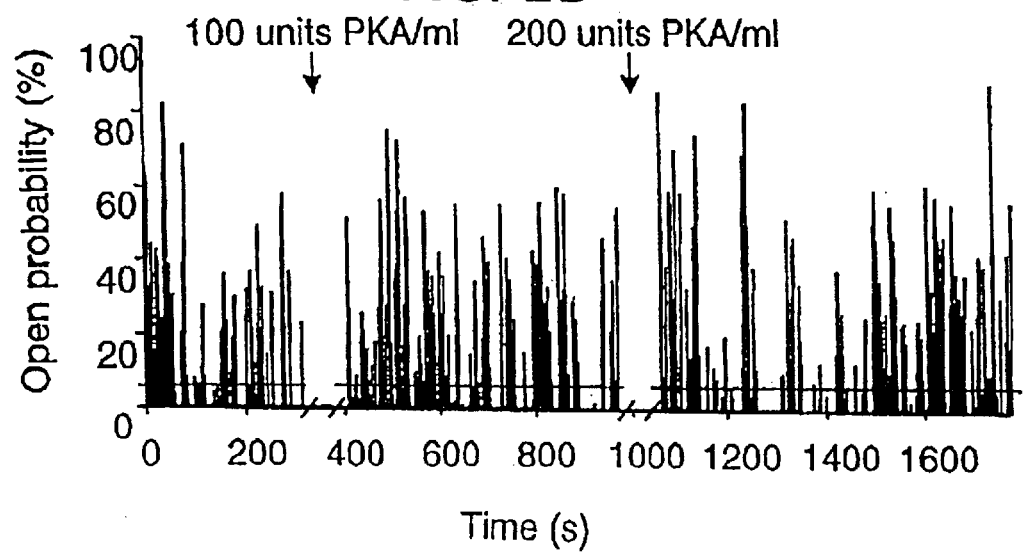

FIG. 2. ΔNEG2-CFTR Forms a Chloride Channel that is Unregulated by PKA (FIG. 2A) Single channel currents of wt, ΔNEG1- and ΔNEG2-CFTR incorporated into the lipid bilayer. While activities of wt-and ΔNEG1-CFTR absolutely require the presence of PKA in the cis-intracellular solution, the ΔNEG2-CFTR channel opens without PKA phosphorylation.

(FIG. 2B) Diary plot of ΔNEG2-CFTR channel open probability versus time shows that addition of 200 units/ml of PKA, a maximally stimulating concentration, does not affect channel activity. The dashed line indicates the average open probability for each segment of the experiment. Channels were recorded at −100 mV.

Figure 3A:
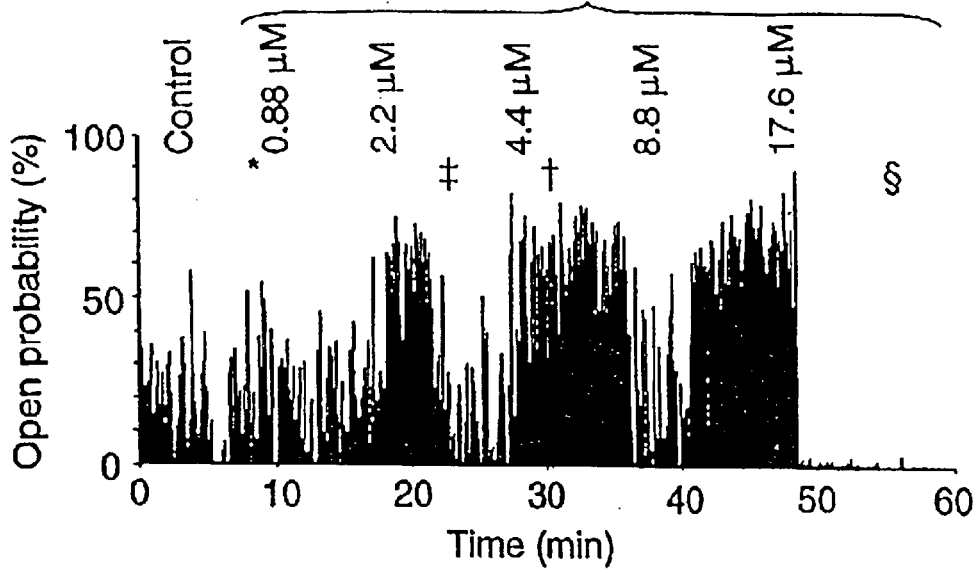

FIG. 3. The Synthetic NEG2 Peptide both Stimulates and Inhibits CFTR (FIG. 3A) Diary plot (open probability versus time) of a wt-CFTR channel illustrating the effect of the NEG2 peptide on the open probability of the channel in the planar lipid bilayer. The concentration of synthetic NEG2 in the cis-intracellular solution is indicated above the plot.

(FIG. 3B) Single channel currents from the wt-CFTR channel were acquired at −80 mV at the points indicated in A. The cis-intracellular solution contained 2 mM ATP and 50 units PKA/ml.

(FIG. 3C) Single channel trace from ΔNEG2-CFTR incorporated into the lipid bilayer membrane. Traces were acquired at −80 mV. The cis-solution contained 2 mM ATP and no PKA. The top two traces were acquired before synthetic NEG2 peptide addition, with the second trace being an expansion of the first. In the bottom two traces, 0.44 $\mu$M of the NEG2 peptide has been added and stimulation is observed. The closed time visibly decreases after peptide addition.

FIG. 4. NEG2 Enhances CFRR Channel Activity by Increasing the Opening Rate of the Channel Histograms of open and closed events of the wt-CFTR channel at −80 mV were generated without peptide (control, left panel) and with 4.4 $\mu$M NEG2 peptide in the cis-solution (right panel).

(FIG. 4A) The open time histograms contain a single exponential component with a time constant of 124 ms (control) and 105 ms (peptide-stimulated).

(FIG. 4B) The closed time histograms contain a fast component and multiple slow components.

(FIG. 4C) The closed-burst duration histograms were constructed using a delimiter of 40 ms (represented by the arrow in B). The solid lines in C represent the fit according to the double exponential equation $y=P_2*\exp[t-\alpha-e_2 x p \alpha t-\alpha)]_2+P_3*\exp[t-\alpha_3-\exp(t-\alpha_3)]$ where $\alpha_2=\log \tau_{c2} \alpha_3=\log \tau_{c3} P_2=$probability of the intermediate closed component, and $P_3=$probability of the long closed component. The best fit parameters are $P_2=0.811$, $\tau_{c2}=459$ ms, $P_3=0.189$, $\tau_{c3}=2494$ ms (control); $P_2=0.957$, $\tau_{c2}=105$ ms, $P_3=0.043$, $\tau_{c3}=1652$ ms (peptide-stimulated).

DETAILED DESCRIPTION OF THE INVENTION

It is a discovery of the present inventors that negatively charged amino acids at the carboxyl terminal of the R domain (817–838, NEG2) is involved in both the stimulatory and inhibitory functions of the R domain on the chloride channel. Moreover, a polypeptide which contains this portion of the CFTR amino acid sequence can be used to enhance the open probability of both wild-type and minimally active mutant CFTR protein.

The isolated polypeptide according to the invention consists of a portion of CFTR (cystic fibrosis transmembrane conductance regulator) protein. The portion preferably contains at least 18 amino acids as shown in SEQ ID NO: 1. However, fewer amino acid residues of the sequence may be used if they retain the channel enhancing function described herein for the 18 and 22 residue polypeptides. See also SEQ ID NO: 2. Thus the polypeptide may be from about 10 or 15 amino acid residues up to about 30 or even 100 amino acid residues. An isolated polypeptide may be synthetic or made in a recombinant organism. It may be a proteolytic cleavage product of a larger primary expression product, including full-length, wild-type CFTR. Preferably the polypeptide will be free of full-length CFTR. The polypeptide will preferably be free of other proteins and polypeptides as well. However, it may be desirable that the polypeptide be fused to another polypeptide to provide additional functional properties. For example, fusion to another protein such as keyhole limpet hemocyanin would be used to increase immunogenicity. Another desirable fusion partner is a membrane-penetrating peptide. Such peptides include VP-22 (SEQ ID NO: 3), as well as the peptides shown in SEQ ID NO: 4 and SEQ ID NO: 5. Such peptides can be used to facilitate the uptake by target cells of the polypeptide.

The polypeptides of the present invention can be used to enhance the function of wild-type or minimally active mutant CFTR proteins. The polypeptide functions to decrease the closed time of the channels formed by CFTR. A polypeptide can be applied to the CFTR protein in any context. It can be applied in vitro or in vivo. If in vitro it can be to CFTR in cultured cells or to planar bilayer membranes containing CFTR. If in vivo, the polypeptide can be applied directly to airway epithelial cells. Such application can be by any means known in the art, including but not limited to using a gargle or a nebulizer to deliver aerosolized polypeptide to the target cells. In addition, the peptide can be delivered in an indirect mode, by delivering a gene construct to the airway epithelial cells, which when taken up by the cells causes them to express the polypeptide. The delivery of the polypeptide to the CFTR preferably increases the open probability of the channel formed by the CFTR by at least 25%. More preferably it increases the open probability by at least 50%, at least 75%, at least 100%, at least 125%, at least 150%, or at least 200%.

A CFTR construct comprises a nucleic acid sequence encoding the amino acid sequence shown in SEQ ID NO: 1. A suitable promoter for expression in lung epithelia is also desirable. Many such promoters are known in the art, and any can be used as appropriate for a particular application.

It is believed that the administration of the polypeptide of the present invention will be the most useful in treatment of a class of mutants which produce CFTR proteins which are properly delivered to the plasma membrane but which are only residually or minimally active. Known mutants of CFTR are listed at the following URL address: http file type, www host server, domain name genet.sickkids.on.ca, directory cftr-cgi-bin, subdirectory fulltable. One can determine that a particular CFTR mutant is fully processed and reaches the plasma membrane in a Western blot assay using antibody against CFTR Fully processed mutants achieve mature glycosylation status and appear on the gel as "band C and band B" whereas mutants that are retained in the endoplasmic reticulum are not fully glycosylated and show only "band B". See Example 2, below and FIG. 1C.

The above disclosure generally describes the present invention. A more complete understanding can be obtained by reference to the following specific examples which are provided herein for purposes of illustration only, and are not intended to limit the scope of the invention.

Example 1

Deletion of a Negatively Charged Region (a.a. 817–838) from the R Domain of CFTR Alters PKA-dependent Regulation of the CFTR Channel CFTR contains a large intracellular regulatory (R) domain where multiple PKA phosphorylation sites are located. There are two regions within the R domain that contain a high proportion of negatively charged amino acids, a.a 725–733 (NEG1) and a.a. 817–838 (NEG2). It is possible that these two regions could have allosteric or electrostatic interactions with other regions of CFTR and thus affect its chloride channel function. To test the role of NEG1 and NEG2, two deletion mutants, NEG1-CFTR and NEG2-CFTR, were created. The CFTR mutants were transiently expressed in HEK 293 cells, and their single channel functions were studied using the bilayer reconstitution system. Western blots indicate that both NEG1-CFTR and NEG2-CFTR process normally and traffic to the plasma membrane of HEK 293 cells. Both mutants form functional chloride channels in the bilayer membrane, with single channel conductances similar to the wt-CFTR channel. Like wt-CFTR, opening of NEG1-CFTR requires absolutely PKA phosphorylation and ATP binding/hydrolysis. In contrast to wt-CFTR, opening of NEG2-CFTR does not require PKA phosphorylation. Thus, deletion of NEG2, but not NEG 1, alters PKA-dependent regulation of the CFTR chloride channel. Our data suggest that NEG2 could form a 'putative gating particle' of the CFTR channel possibly through electrostatic and/or allosteric interactions with other domains of CFTR.

Example 2

ΔNEG1- and ΔNEG2-CFTR are Glycosylated

Figure 1C:
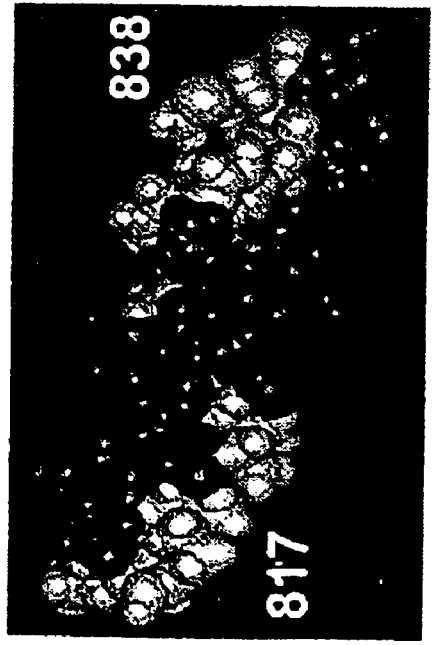

The R domain of CFTR contains two negatively charged regions, amino acids 725–733 (NEG1) and amino acids 817–838 (NEG2), that reside in close proximity to two PKA phosphorylation sites, S737 and S813, used in vivo (FIG. 1A) (Cheng, et al. 1991). NEG2 is predicted to form an amphipathic (-helical structure with a negatively charged face (FIG. 1B) (Geourjon and Deleage, 1995, Rost and Sander, 1993, Rost and Sander, 1994). Three mutations (E822K, E826K, D836Y), two of which were clearly obtained from patients with CF (E822K and D836Y), have been identified within the NEG2 region that result in the removal of negative charges (See URL address: www host server at domain name genet.sickkids.on.ca). The E822K CFTR channel has a low open probability relative to wt-CFTR (wild type-CFTR), but the E826K CFTR channel has single channel properties similar to wt-CFTR (Vankeerberghen et al., 1998). The presence of these disease-causing mutations suggests the potential importance of the NEG2 region. To investigate the roles of NEG1 and NEG2 in CFTR function, these regions were deleted from CFTR using mutagenesis and subcloning. The ΔNEG1- and ΔNEG2-CFTR proteins were transiently expressed in human embryonic kidney 293 cells. Membrane vesicles containing the CFTR proteins were isolated and subjected to SDS-PAGE. Like wt-CFTR, both ΔNEG1- and ΔNEG2-CFTR are present both in the core glycosylated (band B) and the fully glycosylated form (band C) (FIG. 1C).

Example 3

The Open Probability of the ΔNEG2-CFTR Chloride Channel is Much Less than that of Wild Type But is Independent PKA, Although it Contains All PKA Phosphorylation Sites Single channel measurements indicate that the ΔNEG1-CFTR channel is similar to wt-CFTR in its PKA dependence. No chloride channels are observed in the absence of PKA (FIG. 2A) and the open probability in the presence of PKA and ATP is similar to wt-CFTR. In contrast, the ΔNEG2-CFTR channel opens without PKA (FIG. 2A). The constitutive activity of the ΔNEG2-CFTR channel is unlikely to be due to the endogenous phosphorylation of the ΔNEG2-CFTR protein, since protein phosphatase 2A, which decreases activity of the wt-CFTR opened by PKA and ATP (Ma et al., 1997), has no effect on the ΔNEG2-CFTR channel (n=4). Moreover, addition of PKA up to 200 units/ml, four times the concentration required to fully activate wt-CFTR (Ma et al., 1997), does not increase the open probability of the channel (FIG. 2B). ΔNEG2-CFTR has conductance properties similar to wild type (Tao et al., 1996). However, the open probability of the ΔNEG2-CFTR chloride channel is much less than that of wild type and cannot be increased by PKA ($P_0$=0.035 (0.012and $P_0$=0.026 (0.013 without and with PKA respectively, n=5). While NEG2 may represent an inhibitory region, removal of these amino acids does not result in a fully activated channel. The failure of the ΔNEG2-CFTR channel to respond to PKA does not result from inability of the channel to be phosphorylated, for an in vitro assay using ($-^{32}$P-ATP showed comparable phosphorylation of wt-CFTR and ΔNEG2-CFTR (FIG. 1C). Thus, it appears that removal of NEG2 from CFTR completely eliminates the PKA dependence of the chloride channel, although the ΔNEG2-CFTR channel still contains all ten PKA sites and can be phosphorylated.

Example 4

Figure 3B:
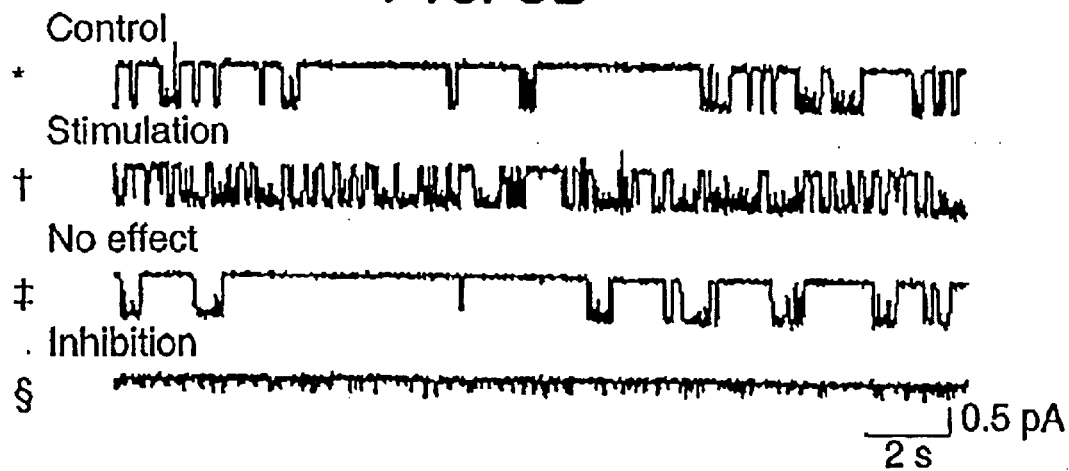
Figure 3C:
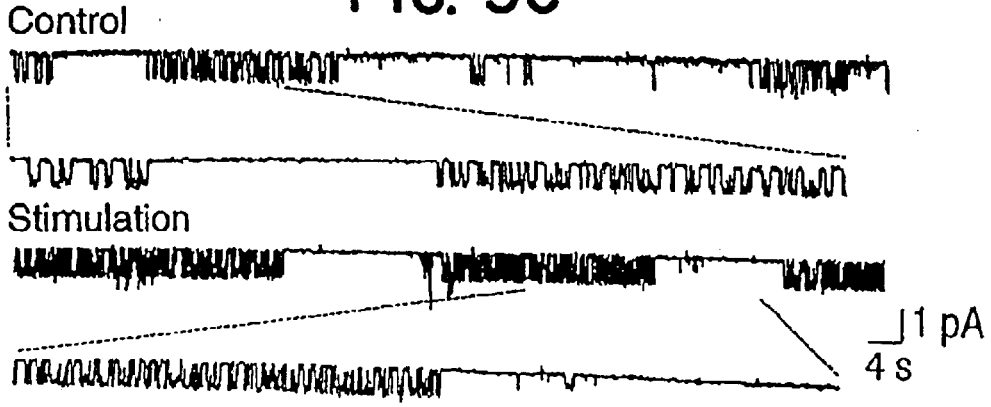

NEG2 Polypeptide Stimulates Both Wild-type and ΔNEG2 CFTR Proteins at Concentrations Greater than 0.44 μM To test whether the NEG2 region is responsible for both stimulatory and inhibitory interactions between the R domain and other domains, synthetic NEG2, a 22 amino acid peptide, was added to the cis-intracellular side of single CFTR channels captured in the planar lipid bilayer (FIG. 3). The diary plot of open probability as a function of time shows the activity of a single wt-CFTR channel during the course of the experiment (FIG. 3A). After peptide addition, there are periods of intense stimulation that last 4 to 8 minutes. These stimulatory periods are followed by either a return to the basal level of activity before peptide addition, or by an almost complete inhibition of the channel, where only a flickery 3 pS conductance is observed. During stimulation, the open probability more than doubles and more transitions are observed between the open and closed states (FIG. 3B). The stimulatory response was observed in 6 of 7 experiments at concentrations $\geq 0.44$ μM (the remaining channel was inhibited upon peptide addition (4.4 μM) and no stimulation was seen). Profound inhibition was observed in three channels at concentrations $\geq 4.4$ μM. When the NEG2 peptide was added to the intracellular side of the ΔNEG2-CFTR channel, which lacks its own endogenous NEG2 sequence, a similar stimulatory response was observed (FIG. 3C).

Example 5

The NEG2 Peptide Decreases the Closed Time of the Wild-type CFTR Protein

Figure 4A:
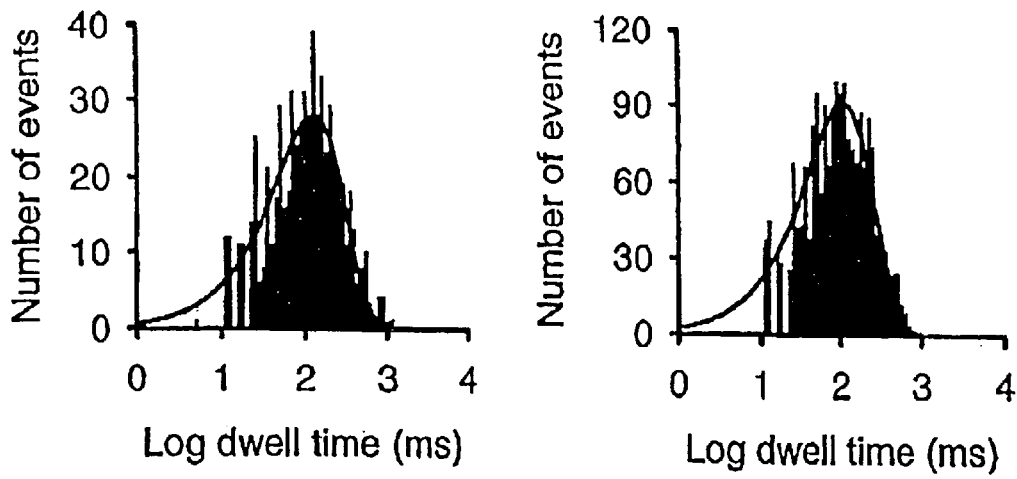
Figure 4B:
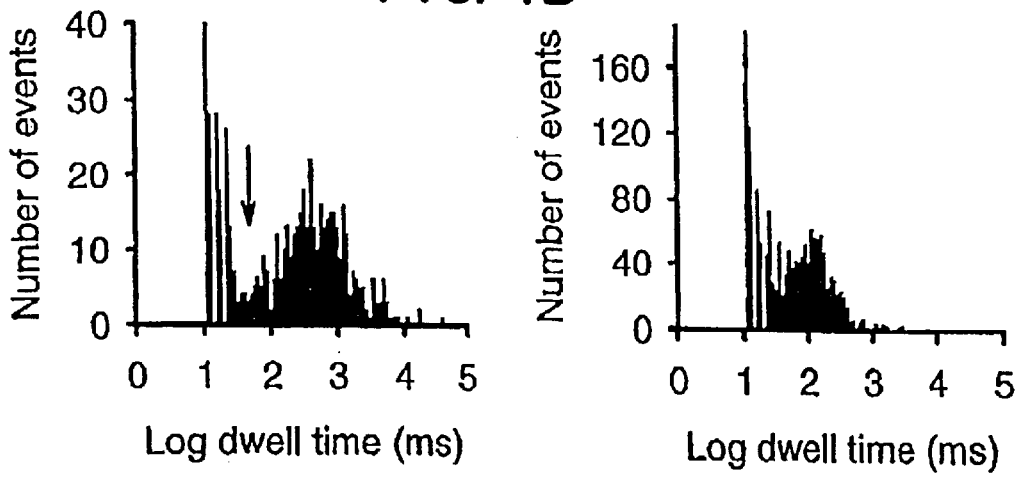
Figure 4C:
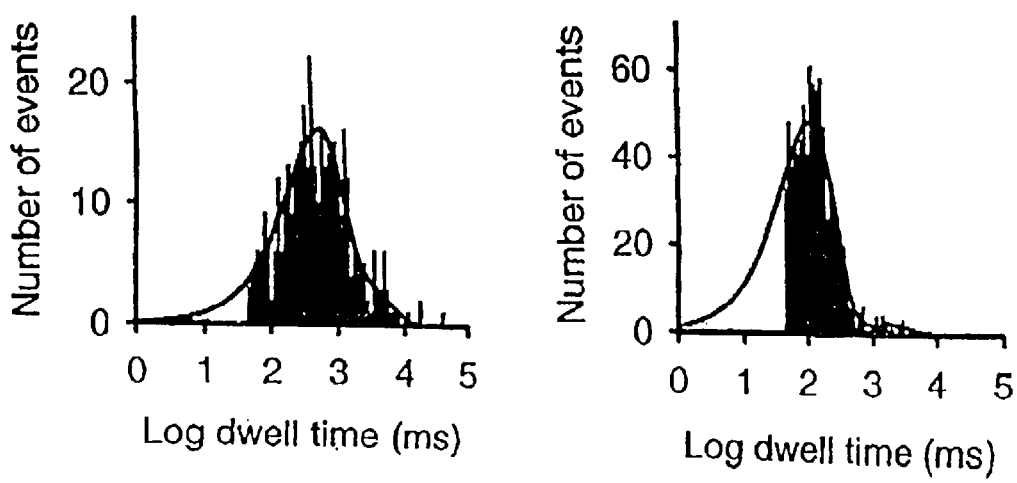

In order to understand the mechanism responsible for the increase in open probability, the gating kinetics of wt-CFTR without peptide and during stimulation by synthetic NEG2 were analyzed. The open time distributions of the wt-CFTR did not change during peptide stimulation, as both control (without NEG2 peptide) and peptide-stimulated channels had an open lifetime of approximately 120 ms (FIG. 4A). Thus, the increase in the open probability is not due to a change in the closing rate of the channel. However, the closed time distribution for the stimulated channel is clearly shifted to the left compared to the control channel (FIG. 4B). There are three components to the closed state, a fast ($\tau_{c1}$), an intermediate ($\tau_{c2}$) and a long ($\tau_{c3}$) closed component. The fast closed component is probably due to closings within a burst (Carson et al., 1995). Therefore, to identify better the closed times between bursts, a delimiter of $\tau_c=40$ ms was set at the nadir between the fast and intermediate closed times (illustrated by the arrow in FIG. 4B) to generate the closed-burst duration histograms. As shown in FIG. 4C, following peptide stimulation, the intermediate closed time was reduced from 459 ms to 105 ms, whereas the long closed time remained relatively unchanged. Thus, the interaction of NEG2 with CFTR increased the intermediate-opening rate of the channel. This increase in opening rate is similar to that observed when the phosphorylated R domain protein (amino acids 645–834) was added to CFTR-ΔR/S660A in excised, inside-out patches (Winter and Welsh, 1997). Additionally, modification of C832, which resides within NEG2, by N-ethylrnaleimide (NEM) results in irreversible stimulation of PKA-phosphorylated CFTR chloride channel activity (Cotten and Welsh, 1997), further emphasizing the importance of NEG2 in CFTR regulation.

These data, taken together, show that the NEG2 region confers both stimulatory and inhibitory functions of the R domain on the CFTR channel. When this region is deleted from CFTR, the resultant channel opens without PKA (loss of inhibitory function), but it never achieves open probability comparable to wild type even when phosphorylated with PKA (loss of stimulatory function). This same sequence, expressed as a peptide, results in stimulation of channel openings at lower concentrations and profound inhibition of channel activity at higher concentrations, when added to the intracellular side of CFTR channels. It seems likely that this sequence interacts with CFTR at different sites on the nucleotide binding domains to either stimulate or inhibit channel openings. Phosphorylation of the R domain, in this model, changes its conformation and thus presents the NEG2 sequence better to the stimulatory than the inhibitory site. A current model for channel opening is that phosphorylated channels open in response to ATP binding and hydrolysis at the first nucleotide binding fold (NBF1) (Gadsby and Nairn, 1994, Ma and Davis, 1998). Since stimulation by NEG2 occurs by increasing channel openings, a likely site of stimulation is NBF1, though other models are possible.

Methods Used in Examples 1–5

Subcloning of CFTR Gene

The wt, ΔNEG1, and ΔNEG2-CFTR cDNAs were subcloned into an Epstein-Barr virus-based episomal eukaryotic expression vector, pCEP4 (Invitrogen, San Diego, Calif.), between the NheI and xhoI restriction sites. The ΔNEG1 and ΔNEG2 deletion mutants were created using the pALTER mutagenesis system and shuttled from pALTER into pCEP4 by substituting the corresponding fragment in pCEP4 wt-CFTR with the mutant fragment between the XhoI and BstZ171 restriction sites. The ΔNEG1-CFTR cDNA has 27 bases deleted (amino acids 725–733). The ΔNEG2-CFTR cDNA has 66 bases deleted (amino acids 817–838).

Expression of CFTR in HEK 293 Cells

A human embryonic kidney cell line (293-EBNA HEK; Invitrogen) was used for transfection and expression of the CFTR proteins (Ma et al., 1997, Ma et al., 1996, Xie et al., 1995). The HEK-293 cell line contains a pCMV-EBNA vector, which constitutively expresses the Epstein-Barr virus nuclear antigen-1 (EBNA-1) gene product and increases the transfection efficiency of Epstein-Barr virus-based vectors. The cells were maintained in Dulbecco's Modified Eagle Medium with 10% FBS and 1% L-glutamine. Geneticin (G418, 250 (g/ml) was added to the cell culture medium to maintain selection of the cells containing the pCMV-EBNA vector. Lipofectamine reagent (Life Technologies, Inc) in Optimem media (serum-free) was used to transfect the HEK-293 cells with pCEP4(wt), pCEP4(ΔNEG1), or pCEP4(ΔNEG2). After 5 hours, serum was added to the media (10% final serum concentration). Twenty-four hours after transfection, the transfection media was replaced with fresh media. The cells were harvested two days after transfection and microsomal membrane vesicles were prepared for single channel measurements in the lipid bilayer reconstitution system.

Vesicle Preparation from Transfected HEK 293 Cells

HEK-293 cells transfected with pCEP4(CFTR) were harvested and homogenized using a combination of hypotonic lysis and Dounce homogenization in the presence of protease inhibitors (Ma et al., 1997, Ma et al., 1996, Xie et al., 1995). Microsomes were collected by centrifugation of postnuclear supernatant (4500×g, 15 min) at 100,000×g for 20 min and resuspended in a buffer containing 250 mM sucrose, 10 mM HEPES, pH 7.2. The membrane vesicles were stored at −75° C. until use.

In Vitro Phosphorylation of CFTR Proteins

CFTR proteins isolated in membrane vesicles were bound to protein G agarose using a mouse monoclonal anti-human CFTR antibody (Genzyme). The protein G agarose was washed, and (-$^{32}$P-ATP (10(Ci) and protein kinase A (~10 units/50(l) was added. Samples were incubated at 30(C for one hour during phosphorylation. Excess ($\gamma$-$^{32}$P-ATP was removed, and SDS-PAGE sample buffer (200 mM TrisCl, pH 6.7,9% SDS, 6% beta-mercaptoethanol, 15% glycerol, and 0.01% bromophenol blue) was added to denature CFTR and release it from the protein G agarose. The samples were subjected to electrophoresis on a 5% SDS-polyacrylamide gel, transferred to a polyvinylidene difluoride membrane, and exposed to film.

Preparation of NEG2 Peptides

The 22 amino acid peptide corresponding to NEG2 was custom made by Quality Controlled Biochemicals, Inc. The peptide was resuspended in water to a concentration of 1 mg/ml and pH was adjusted to a physiological range (7.2–7.4) using KOH and HCl. The space filling model of the NEG2 peptide was generated, based on secondary structure predictions (Geouron and Deleage, 1995, Rost and Sander, 1993, Rost and Sander, 1994), using the Insight II program from Molecular Simulations Incorporated.

Reconstitution of CFTR Channels in Lipid Bilayer Membranes

Lipid bilayer membranes were formed across an aperture of ~200 (m diameter with a mixture of phosphatidylethanolamine:phosphatidylserine:cholesterol in a ratio of 5:5:1. The lipids were dissolved in decane at a concentration of 33 mg/ml. The recording solutions contained: cis (intracellular), 200 mM CsCl, 1 mM MgCl$_2$, 2 mM ATP, and 10 mM HEPES-Tris (pH 7.4); trans (extracellular), 50 mM CsCl, 10 mM HEPES-Tris (pH 7.4). Vesicles (1–4 (l) containing either wild-type, $\Delta$NEG1-, or $\Delta$NEG2-CFTR were added to the cis solution. The PKA catalytic subunit was present at a concentration of 50 units/ml in the cis solution unless noted otherwise. Single channel currents were recorded with an Axopatch 200A patch clamp unit (Axon Instrnments). The currents were sampled at 1–2.5 ms/point. Single channel data analyses were performed with pClamp and TIPS softwares.

References

Anderson, M. P., Berger, H. A., Rich, D. P., Gregory, R. J., Smith, A. E., and Welsh, M. J. (1991). Nucleoside triphosphates are required to open the CFTR chloride channel. Cell 67, 775–784.

Bear, C. E., Li, C., Kartner, N., Bridges, R. J., Jensen, T. J., Rarnjeesingh, M., and Riordan, J. R. (1992). Purification and functional reconstitution of the cystic fibrosis transmembrane conductance regulator (CFTR). Cell 68, 809–818.

Carson, M. R., Travis, S. M., and Welsh, M. J. (1995). The two nucleotide-binding domains of cystic fibrosis transmembrane conductance regulator (CFTR) have distinct functions in controlling channel activity. J. Biol. Chem. 270, 1711–1717.

Cheng, S. H., Rich, D. P., Marshall, J., Gregory, R. J., Welsh, M. J., and Smith, A. E. (1991). Phosphorylation of the R domain by cAMP-dependent protein kinase regulates the CFTR chloride channel. Cell 66, 1027–1036.

Cotten, J. F. and Welsh, M. J. (1997). Covalent modification of the regulatory domain irreversibly stimulates cystic fibrosis transmembrane conductance regulator. J. Biol. Chem. 272, 25617–25622.

Dulhanty, A. M. and Riordan, J. R. (1994). Phosphorylation by cAMP-dependent protein kinase causes a conformational change in the R domain of the cystic fibrosis transmembrane conductance regulator. Biochemistry 22, 4072–4079.

Gadsby, D. C. and Nairn, A. C. (1994). Regulation of CFTR channel gating. Trends Biochem. Sci. 19, 513–518.

Geourjon, C. and Deleage, G. (1995). SOPMA: significant improvements in protein 20 secondary structure prediction by consensus prediction from multiple alignments. CABIOS 11, 681–684.

Gunderson, K. L. and Kopito, R. R. (1995). Conformational states of CFTR associated with channel gating: the role of ATP binding and hydrolysis. Cell 82, 231–239.

Higgens, C. F. (1992). ABC transporters: from microorganisms to man. Annu. Rev. Cell Biol. 8, 67–113.

Ma, J. and Davis, P. B. (1998). What we know and what we do not know about cystic fibrosis transmembrane conductance regulator. Clinics in Chest Medicine 19, 459–471.

Ma, J., Tasch, J. E., Tao, T., Zhao, J., Xie, J., Drumm, M. L., and Davis, P. B. (1996). Phosphorylation-dependent block of cystic fibrosis transmembrane conductance regulator chloride channel by exogenous R domain protein. J. Biol. Chem. 271, 7351–7356.

Ma, J., Zhao, J., Drumm, M. L., Xie, J., and Davis, P. B. (1997). Function of the R domain in the cystic fibrosis transmembrane conductance regulator chloride channel. J. Biol. Chem. 272, 28133–28141.

Picciotto, M. R., Cohn, J. A., Bertuzzi, G., Greengard, P., and Nairn, A. C. (1992). Phosphorylation of the cystic fibrosis transmembrane conductance regulator. J. Biol. Chem. 267, 12742–12752.

Quinton, P. M. (1986). Missing Cl conductance in cystic fibrosis. Am. J. Physiol. 251, C649–C652.

Rich, D. P., Berger, H. A., Cheng, S. H., Travis, S. M., Saxena, M., Smith, A. E., and Welsh, M. J. (1993). Regulation of the cystic fibrosis transmembrane conductance regulator Cl channel by negative charge in the R domain. J. Biol. Chem. 268, 20259–20267.

Rich, D. P., Gregory, R. J., Anderson, M. P., Manavalan, P., Smith, A. E., and Welsh, M. J. (1991). Effect of deleting the R domain on CFTR-generated chloride channels. Science 253, 205–207.

Riordan, J., Rommens, J., Kerem, B.-S., Noa, A., Rozmahel, R., Grzelczak, Z., Zielenski, J., Lok, S., Plavsic, N., Chou, J.-L., Drumm, M., Iannuzzi, M., Collins, F., and Tsui, L.-C. (1989). Identification of the cystic fibrosis gene: cloning and characterization of complementary DNA. Science 245, 1066–1073.

Rost, B. and Sander, C. (1993). Prediction of protein structure at better than 70% accuracy. J. Mol. Biol. 232, 584–599.

Rost, B. and Sander, C. (1994). Combining evolutionary information and neural networks to predict protein secondary structure. Proteins 19, 55–72.

Tabcharani, J. A., Chang, X.-B., Riordan, J. R. and Hanrahan, J. W. (1991). Phosphorylation-regulated Cl-channel in CHO cells stably expressing the cystic fibrosis gene. Nature 352, 628–631.

Tao, T., Xie, J., Drumm, M. L., Zhao, J., Davis, P. B., and Ma, J. (1996). Slow conversions among subconductance states of cystic fibrosis transmembrane conductance regulator chloride channel. Biophys. J. 70, 743–753.

Vankeerberghen, A., Wei, L., Jaspers, M., Cassiman, J.-J., Nilius, B., and Cuppens, H. (1998). Characterization of 19 disease-associated missense mutations in the regulatory domain of the cystic fibrosis transmembrane conductance regulator. Hum. Mol. Genet. 7, 1761–1769.

Welsh, M. J. and Smith, A. E. (1993). Molecular mechanisms of CFTR chloride channel dysfunction in cystic fibrosis. Cell 73, 1251–1254.

Winter, M. C. and Welsh, M. J. (1997). Stimulation of CFTR activity by its phosphorylated R domain. Nature 389, 294296.

Xie, J., Drumm, M. L., Ma, J., and Davis, P. B. (1995). Intracellular loop between transmembrane segments IV and V of cystic fibrosis transmembrane conductance regulator is involved in regulation of chloride channel conductance state. J. Biol. Chem. 270, 28084–28091.

Zielenski, J. and Tsui, L. C. (1995). Cystic fibrosis: genotypic and phenotypic variations. Annu. Rev. Genetics 29, 777–807.

What is claimed is:

1. An isolated polypeptide consisting of a portion of CFTR (cystic fibrosis transmembrane conductance regulator) protein wherein said portion consists of between 18 and 100 amino acid residues, wherein said portion comprises 18 amino acid residues as shown in SEQ ID NO: 1.

2. The polypeptide of claim 1 wherein the portion of CFTR protein comprises 22 amino acid residues as shown in SEQ ID NO: 2.

3. The polypeptide of claim 1, wherein the portion of CFTR protein consists of a sequence of amino acid residues as shown in SEQ ID NO: 2, and wherein the portion is free of phosphorylation.

4. An isolated fusion protein consisting of:
   a portion of CFTR protein wherein said portion consists of between 18 and 100 amino acid residues, and wherein said portion comprises 18 amino acid residues as shown in SEQ ID NO:1; and
   a polypeptide which provides an additional functional property.

5. The polypeptide of claim 4 wherein the polypeptide is a membrane-penetrating peptide.

6. The polypeptide of claim 5 wherein the membrane-penetrating peptide is selected from the group consisting of: VP-22 (SEQ ID NO: 3), (SEQ ID NO: 4), and (SEQ ID NO: 5).

7. The isolated fusion protein of claim 4 wherein the portion of CFTR protein comprises 22 amino acid residues as shown in SEQ ID NO:2.

8. The polypeptide of claim 7 wherein the polypeptide is a membrane-penetrating peptide.

9. The polypeptide of claim 8 wherein the membrane-penetrating peptide is selected from the group consisting of: VP-22 (SEQ ID NO: 3), (SEQ ID NO: 4), and (SEQ ID NO: 5).

* * * * *